United States Patent [19]

Takigawa et al.

[11] Patent Number: 5,302,522

[45] Date of Patent: Apr. 12, 1994

[54] PROCESS FOR THE PRODUCTION OF SEC-CEDRENOL AND CEDRENONE FROM ALPHA-CEDRENE BY RHODOCOCCUS

[75] Inventors: Hirofumi Takigawa, Tochigi; Hiromi Kubota, Tokyo; Susumu Ito; Yoshiaki Fujikura, both of Tochigi; Shigeyoshi Tanaka, Wakayama, all of Japan

[73] Assignee: Kao Corporation, Tokyo, Japan

[21] Appl. No.: 111,888

[22] Filed: Aug. 26, 1993

Related U.S. Application Data

[62] Division of Ser. No. 861,749, Apr. 1, 1992.

[30] Foreign Application Priority Data

| Apr. 2, 1991 [JP] | Japan | 3-94918 |
| Jun. 4, 1991 [JP] | Japan | 3-159540 |
| Jul. 9, 1991 [JP] | Japan | 3-193578 |

[51] Int. Cl.$^5$ .................... C12P 15/00; C12N 1/20
[52] U.S. Cl. .................... 435/127; 435/155; 435/280; 435/252.1
[58] Field of Search ............ 435/127, 155, 280, 252.1

[56] References Cited

U.S. PATENT DOCUMENTS

4,745,064  5/1988  Cook et al. .................. 435/252.1

FOREIGN PATENT DOCUMENTS

0114188  6/1985  Japan .................. 435/252.1
0114189  6/1985  Japan .................. 435/252.1

OTHER PUBLICATIONS

Nakajima et al, "Microbial Metabolism of Isoprenoid Alkane Pristane", *Nippon Nogeikagaku Kaishi*, vol. 57, No. 4, pp. 299–305, 1983.
ATCC Catalogue of Bacteria and Bacteriophages, vol. 17, pp. 184–187, 1989.

*Primary Examiner*—Marian Knode
*Attorney, Agent, or Firm*—Sughrue, Mion, Zinn, Macpeak & Seas

[57] ABSTRACT

A biological pure culture of a microorganism belonging to the genus Rhodococcus and being capable of oxidizing the allyl position of α-cedrene, a process for producing sec-cedrenol comprising contacting a microorganism belonging to the genus Rhodococcus with α-cedrene, and a process for producing cedrenone comprising oxidizing sec-cedrenol produced by a microorganism belonging to the genus Rhodococcus, are disclosed. According to the process of the present invention, sec-cedrenol can be produced efficiently within a short period of time and with high purity. In addition, the process of the present invention can produce cedrenone with a high yield in a large quantity within a short period of time.

3 Claims, 6 Drawing Sheets

PROCESS FOR THE PRODUCTION OF SEC-CEDRENOL AND CEDRENONE FROM ALPHA-CEDRENE BY RHODOCOCCUS

This is a divisional of application Ser. No. 07/861,749 filed Apr. 1, 1992.

FIELD OF THE INVENTION

This invention relates to a biologically pure culture of a microorganism belonging to the genus Rhodococcus, particularly to a biologically pure culture of a microorganism belonging to the genus Rhodococcus and being capable of converting α-cedrene into sec-cedrenol by specifically oxidizing the allyl position of α-cedrene.

This invention also relates to a novel process for producing sec-cedrenol which has a vasodilation function and is useful as an intermediate product of the process for producing cedrenone, particularly to a process for producing sec-cedrenol in which a microorganism belonging to the genus Rhodococcus is employed.

This invention further relates to a process for producing cedrenone, particularly to a process for producing cedrenone which has a vasodilation function and is useful as a component of bathing preparations, hair tonics, skin care cosmetics, stomatic preparations and the like.

BACKGROUND OF THE INVENTION

Cedrenone is a known sesquiterpene compound represented by the following formula (I):

(I)

and can be obtained by chromic acid oxidation of α-cedrene represented by the following formula (III):

(III)

or by autoxidation of α-cedrene using cobalt resinate as disclosed, for example, in Kato, *Perfume*, No. 123, p. 31 (1978).

Each of these prior art cedrenone production processes, however, has disadvantages in that it requires not only a prolonged period of reaction time but also complicated handling for the separation of the resulting cedrenone due to many by-products. Especially, a method for producing sec-cedrenol, which is an intermediate product of the process for producing cedrenone, in a large scale has not been established and thus these processes are not satisfactory from an industrial viewpoint.

That is, sec-cedrenol represented by the following formula (II):

(II)

is a sesquiterpene alcohol which does not exist in nature and only one method has been known for providing sec-cedrenol, which method comprises chemically converting α-cedrene, which exists in a cedar wood oil, in the presence of a resin acid as disclosed in Blumann et al., *Ber.* vol. 62, p. 1698 (1929) which is an oxidation catalyst, as disclosed, for example, in Kato, *Perfume*, No. 123, p. 31 (1978).

This process, however, is not industrially useful because of disadvantages in that it requires not only a prolonged period of reaction time but also complicated handling for the separation of the resulting sec-cedrenol due to many by-products.

Recently, it has been reported that sec-cedrenol and cedrenone have a vasodilation function as disclosed, for example, in Japanese Patent Application No. Hei-3-145236, and studies on the application of these compounds have been started. However, an industrially advantageous process for producing sec-cedrenol and cedrenone must be developed to use sec-cedrenol and cedrenone in various applications.

SUMMARY OF THE INVENTION

The inventors of the present invention have conducted extensive studies on an advantageous production of sec-cedrenol from α-cedrene and found that a microorganism belonging to the genus Rhodococcus, which has been isolated from a soil sample collected at a place in Wakayama Prefecture, Japan, is possessed of a function to selectively convert α-cedrene into sec-cedrenol with a high yield. The present invention has been accomplished on the basis of this finding.

In addition, the inventors of the present invention have also conducted extensive studies on the production of cedrenone and found that cedrenone can be obtained industrially advantageously by oxidizing sec-cedrenol prepared from α-cedrene using a microbial reaction. The present invention has also been accomplished on the basis of this finding.

Accordingly, an object of the present invention is to provide a biologically pure culture of a microorganism belonging to the genus Rhodococcus and being capable of oxidizing the allyl position of α-cedrene.

Another object of the present invention is to provide a process for producing sec-cedrenol which comprises contacting a microorganism belonging to the genus Rhodococcus with α-cedrene.

A further object of the present invention is to provide a processe for producing cedrenone which comprises oxidizing sec-cedrenol produced by a microorganism belonging to the genus Rhodococcus.

Other objects and advantages of the present invention will be made apparent as the description progresses.

DETAILED DESCRIPTION OF THE INVENTION

Techniques for contacting a microorganism belonging to the genus Rhodococcus with α-cedrene are not particularly limited. For example, sec-cedrenol may be obtained by culturing the microorganism in a medium containing α-cedrene, or by contacting resting cells, immobilized cells, disintegrated cells or the like of the microorganism with α-cedrene. Alternatively, sec-cedrenol may efficiently be obtained by contacting the cells with α-cedrene repeatedly.

A microorganism belonging to the genus Rhodococcus to be used in the present invention has a function to oxidize the allyl position of α-cedrene. The following summarizes bacteriological properties of a typical strain, Rhodococcus sp. KSM-7358.

(1) Morphological Characteristics

Rod-shaped cell having a size of 0.8–1.0 μm × 1.0–12 μm, showing pleomorphism. That is, cells become a branched mycelial form at the early stage of culturing, and are subsequently disunited into short rods. The cell is not motile and has no flagella. It is Gram-positive but with no spore formation or acid fastness.

(2) Cultural Properties (a) Nutrient agar plate culture

Good growth of rough-surfaced convex colonies with circular, curled and undulate periphery; milky white and opaque but skin-color or pale orange in the late culture stage.

(b) Nutrient agar slant culture

Good growth of milky white colonies.

(c) Nutrient broth culture

Poor growth but evenly from the surface to lower layers of the liquid medium.

(d) Nutrient-gelatin stab culture

Good growth with no gelatin liquefaction.

(e) Litmus milk

Liquefaction only in the upper layer. Litmus color changes from purple to pink with partial decoloring.

(3) Physiological Characteristics (a) Nitrate reduction: negative (Nitrate broth)
(b) Denitrification: negative
(c) MR test: negative
(d) VP test: negative
(e) Formation of indole: negative
(f) Formation of hydrogen sulfide: slightly positive
(g) Hydrolysis of starch: negative
(h) Utilization of citric acid
  Koser's medium: positive
  Christensen's medium: positive
(i) Utilization of nitrates: positive
(j) Utilization of ammonium salts: positive
(k) Formation of pigments:
  King's medium A: negative
  King's medium B: negative
(l) Urease test: positive
(m) Oxidase test: negative
(n) Catalase test: positive
(o) pH for growth
  pH range: 3 to 10
  optimum pH: 5 to 9.0
(p) Temperature for growth
  range: 10° to 37° C.
  optimum: 25° to 30° C.
(q) Relation to oxygen: aerobic, but full growth under static culture condition.
(r) OF test: slightly oxidation type (detectable with Andrade's solution but not with BTB indicator even after 7 days of culturing)
(s) Growth in NaCl medium: grows in the presence of both 5% and 7% sodium chloride.
(t) Utilization of sugars:

| | |
|---|---|
| L-arabinose | − |
| D-xylose | − |
| D-glucose | + |
| D-mannose | + (weak) |
| D-fructose | + |
| D-galactose | − |
| maltose | + (weak) |
| sucrose | + |
| lactose | − |
| trehalose | + (weak) |
| D-sorbitol | + |
| D-mannitol | + |
| inositol | + |
| glycerol | + (weak) |
| starch | − |
| D-ribose | + |

(Notes;
+: utilized; −: not utilized)

(4) Chemotaxonomical Properties (a) Glycolate test: glycolyl type
(b) Crosslinked amino acid in cell wall: meso-2,6-diaminopimelic acid
(c) Cell wall sugars: arabinose and galactose, but no trace of xylose
(d) Menaquinone system: MK-8 (Hz)

When the taxonomic position of this strain was examined by referring these bacteriological properties to *Bergey's Manual of Systematic Bacteriology* (Vol. 2 (1986)), it was confirmed that the strain KSM-7358 was a microorganism belonging to the genus Rhodococcus.

Since the above bacteriological properties did not coincide with those of known Rhodococcus species or strains, the present inventors have judged this bacterium to be a new strain. This strain has been deposited by the present inventors on Feb. 25, 1991 in Fermentation Research Institute, Agency of Industrial Science and Technology, whose full post address is 1-3, Higashi 1-chome, Tsukuba-shi, Ibaraki, Japan, and has been assigned Fermentation Research Institute Deposition Number FERM P-12039. This deposition has been changed to International Deposition under the Budapest Treaty on Feb. 14, 1992 and assigned International Deposition Number FERM BP-3747.

In the practice of the process of the present invention in which the microorganism capable of oxidizing the allyl position of α-cedrene is used, it is advantageous to increase the number of cells by culturing the microorganism.

A medium suitable for the culturing of the microorganism to be used in the present invention may contain carbon sources including sugars such as fructose, maltose, trehalose, sorbitol, mannitol, glycerol, glucose, sucrose and the like, sesquiterpenes such as cedar oil, α-cedrene and the like, n-alkanes and the like; nitrogen sources such as peptone, yeast extracts, urea, sodium nitrate, ammonium sulfate, amino acids and the like; inorganic salts such as potassium phosphate, magnesium sulfate, calcium chloride and the like; and, if required, appropriate amounts of metal salts such as of $Mn^{2+}$, $Zn^{2+}$, $Ni^{2+}$ and the like and vitamins such as biotin, thiamine and the like. Specific and non-limiting examples of such a medium include Nutrient broth, Soybean-casein-digest and so on.

Though not particularly limited, culturing of the microorganism may be carried out, in general, at a temperature of from 25° to 30° C., at a medium pH of from 5.0 to 9.0 and with aeration by shaking or agitation.

Microbial conversion of α-cedrene by the thus prepared bacterial cells may be effected by (1) adding α-cedrene to a cultured broth containing an increased number of cells and continuing the culturing, (2) preparing resting cells from the cultured broth, suspending the resting cells in an appropriate buffer solution or de-ionized water, adding α-cedrene to the cell suspension and then aerating the resulting mixture by shaking or agitation, or (3) allowing immobilized cells or disrupted cells of the microorganism to contact with α-cedrene.

Preparation of resting cells from a cultured broth may be effected making use of known techniques, for example by washing cultured cells with an appropriate buffer solution or de-ionized water. Specifically, it can be effected by separating cells from a cultured broth by means of centrifugation, filtration or the like and then re-suspending the cells in an appropriate buffer solution or de-ionized water.

When the microorganism of the present invention is cultured in a medium containing α-cedrene, sec-cedrenol is formed firstly as an intermediate compound. In consequence, production of sec-cedrenol may be effected by terminating the culturing when its amount reached maximum and then isolating it from the cultured broth.

In the case of the use of resting cells, sec-cedrenol may also be obtained at a high yield by selecting proper reaction time for the maximum production of the compound of interest.

Thus, sec-cedrenol can be produced efficiently from α-cedrene by employing any of these processes in which the microorganism of the present invention is used.

Though the number of cells to be used in the reaction of the present invention is not particularly limited, the cell suspension may be adjusted to such a concentration that its absorbance at 600 nm reaches a range of from about 20 to about 80. The reaction may be effected at about 100 to 400 rpm of agitation, about 25° to 30° C. of cell suspension temperature and about 24 to 96 hours of reaction time.

Separation and collection of sec-cedrenol from conversion products thus obtained may be effected by employing one or a combination of usually used purification means such as column chromatography, high performance liquid chromatography, crystallization and the like.

Examples of oxidizing agents for use in the oxidation of the thus obtained sec-cedrenol include chromic acid derivatives such as chromic anhydride, dichromate (e.g., sodium dichromate, potassium dichromate), a chromium oxide-pyridine complex, pyridinium chlorochromate, manganese dioxide, dimethyl sulfoxide, a hypo-halogen acid salt (e.g., hypo-halogen acid salt of sodium or t-butyl), a carbonyl compound (e.g., acetone, cyclohexanone) and the like, of which chromic acid derivatives such as chromic anhydride and pyridinium chlorochromate and the like are particularly preferred.

The oxidation reaction may be effected in the presence of such oxidizing agent in an amount of from 1 to 10 moles, preferably from 1 to 3 moles, per 1 mole of sec-cedrenol, in a solvent such as acetone, petroleum ether, hexane, dichloromethane or the like at a temperature of from 15° to 30° C. for a reaction period of 1 to 2 hours.

Separation and collection of cedrenone from the thus obtained reaction mixture may be effected by employing one or a combination of usually used purification means such as column chromatography, high performance liquid chromatography, crystallization and the like.

sec-Cedrenol and cedrenone which can be obtained by the process of the present invention have a vasodilation function and are useful as a component of bathing preparations, hair tonics, skin care cosmetics, stomatic preparations and the like.

According to the process of the present invention, sec-cedrenol can be produced efficiently within a short period of time and with high purity, while the prior art process require a prolonged period of reaction time and cannot prevent formation of by-products. In addition, according to the inventive process, sec-cedrenol can be produced under mild conditions by means of biological catalytic reaction.

The process of the present invention is markedly advantageous from an industrial point of view, because cedrenone can be produced with a high yield in a large quantity within a shorter reaction period in comparison with the prior art processes.

The following examples are provided to further illustrate the present invention.

EXAMPLE 1

A spoonful (about 0.5 to 1 g) of a soil sample collected at Katsuura, Wakayama Prefecture, Japan, was suspended in 10 ml of sterile de-ionized water and further diluted to an appropriate level. The thus diluted soil sample was put in a large test tube containing 10 ml of Medium A as shown below, and the contents were incubated at 30° C. for 5 days with shaking to enrich microorganisms in the sample. A portion of the resulting culture broth was spread on a plate medium which has been prepared by adding 1.5% of agar to Medium A, and the plate was incubated to isolate a strain capable of utilizing α-cedrene. Each of strains capable of utilizing α-cedrene thus isolated was inoculated into a large test tube containing 10 ml of Medium A and cultured at 30° C. for 5 days with shaking. Thereafter, the resulting culture broth was extracted with hexane, and a portion of the hexane-soluble fraction was applied to gas chromatography to determine the amount of compounds formed. As the results, a strain, KSM-7358, was obtained, which is capable of utilizing α-cedrene and producing sec-cedrenol.

| Medium A: | |
|---|---|
| $Na_2SO_4$ | 0.71 g |
| $NH_4NO_3$ | 3.5 g |
| $FeCl_3.6H_2O$ | 0.01 g (separately sterilized) |

-continued

| Medium A: | |
|---|---|
| MgCl$_2$.6H$_2$O | 0.17 g (separately sterilized) |
| CaCl$_2$.2H$_2$O | 0.1 g (separately sterilized) |
| α-Cedrene | 10 g (aseptic separate addition) |

Fill up to 1 liter with 50 mM phosphate buffer (pH 7).

EXAMPLE 2

Figure 1:
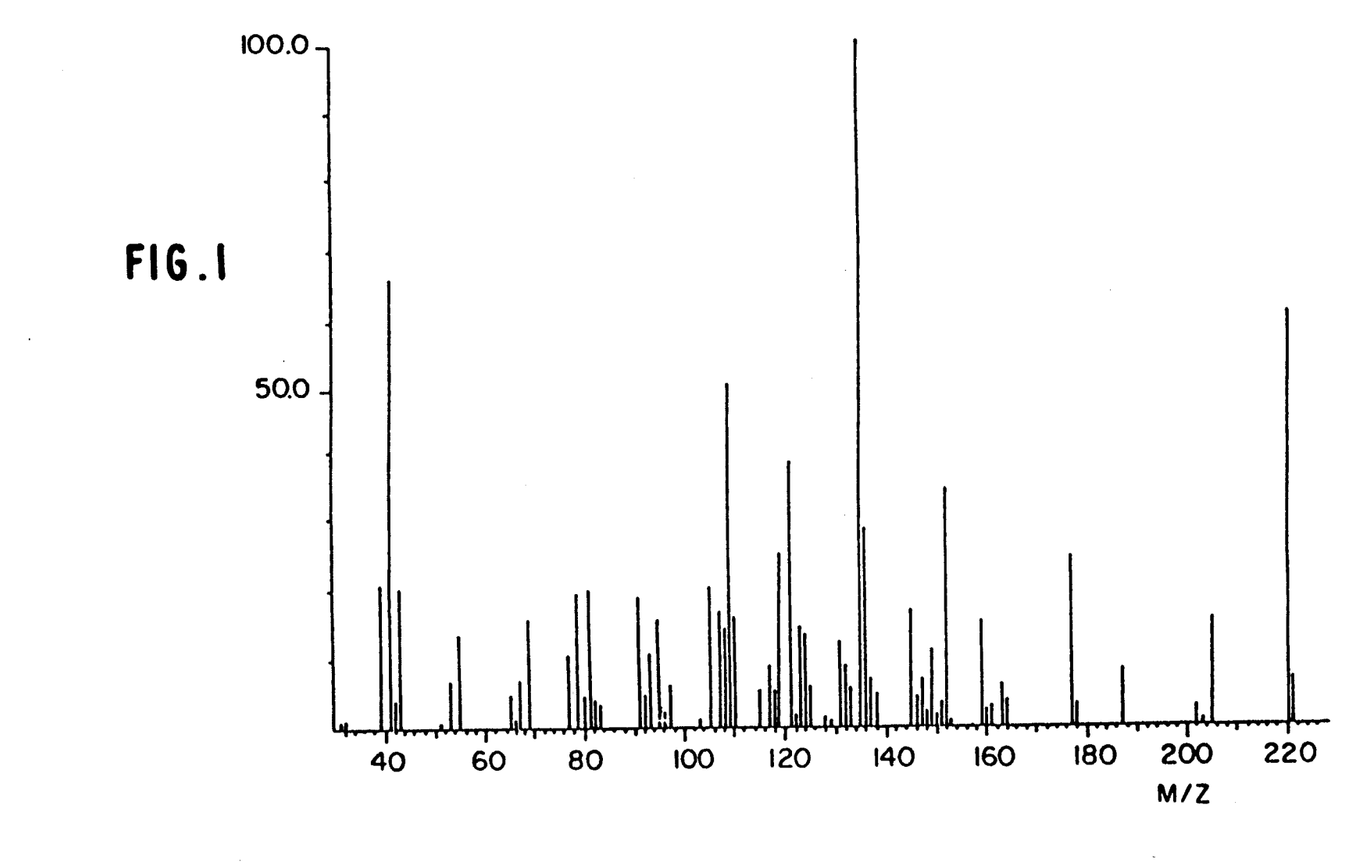
FIG. 1 is a graph showing EI-MS spectrum of sec-cedrenol.
Figure 2:
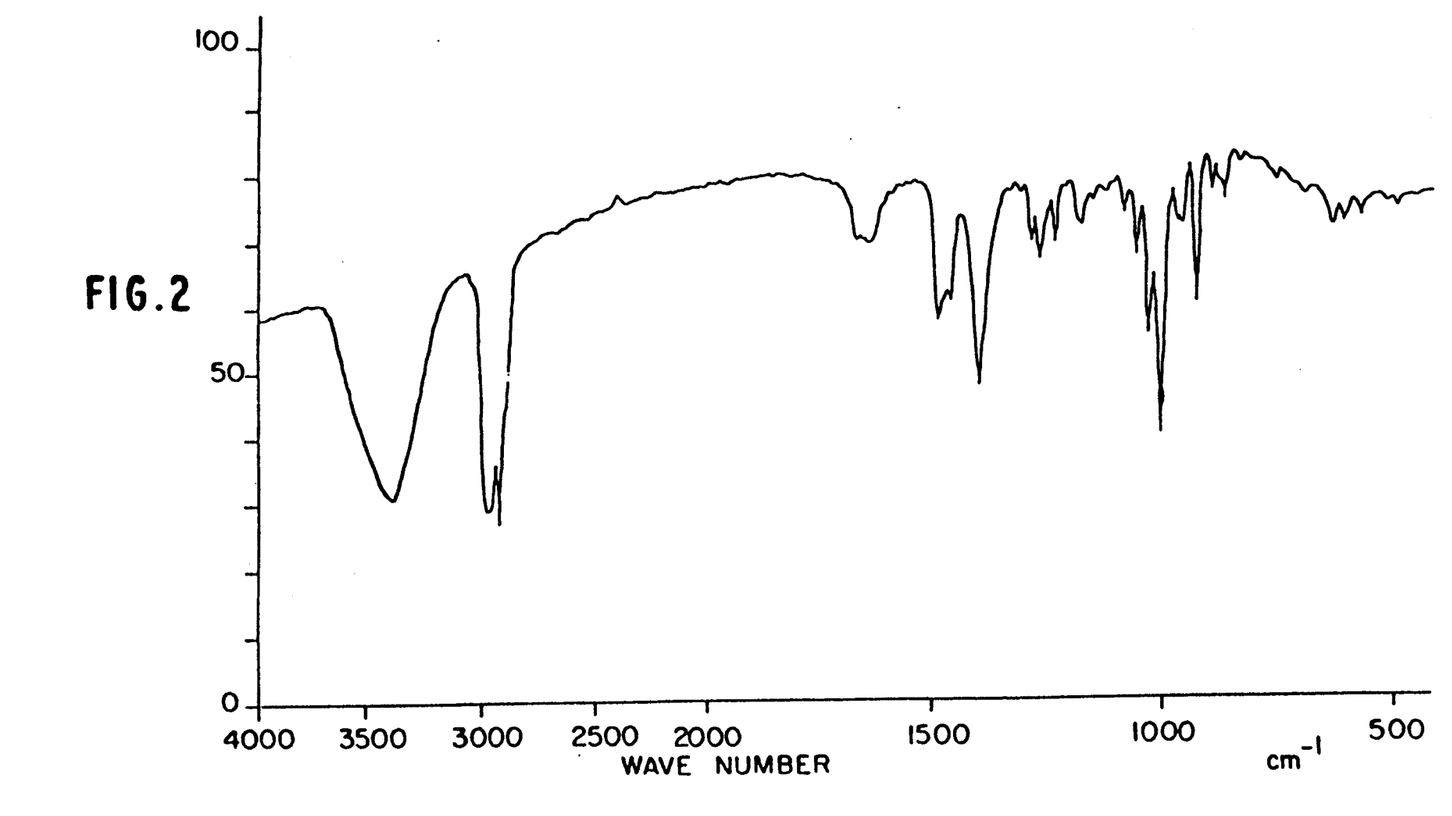
FIG. 2 is a graph showing IR spectrum of sec-cedrenol.
Figure 3:
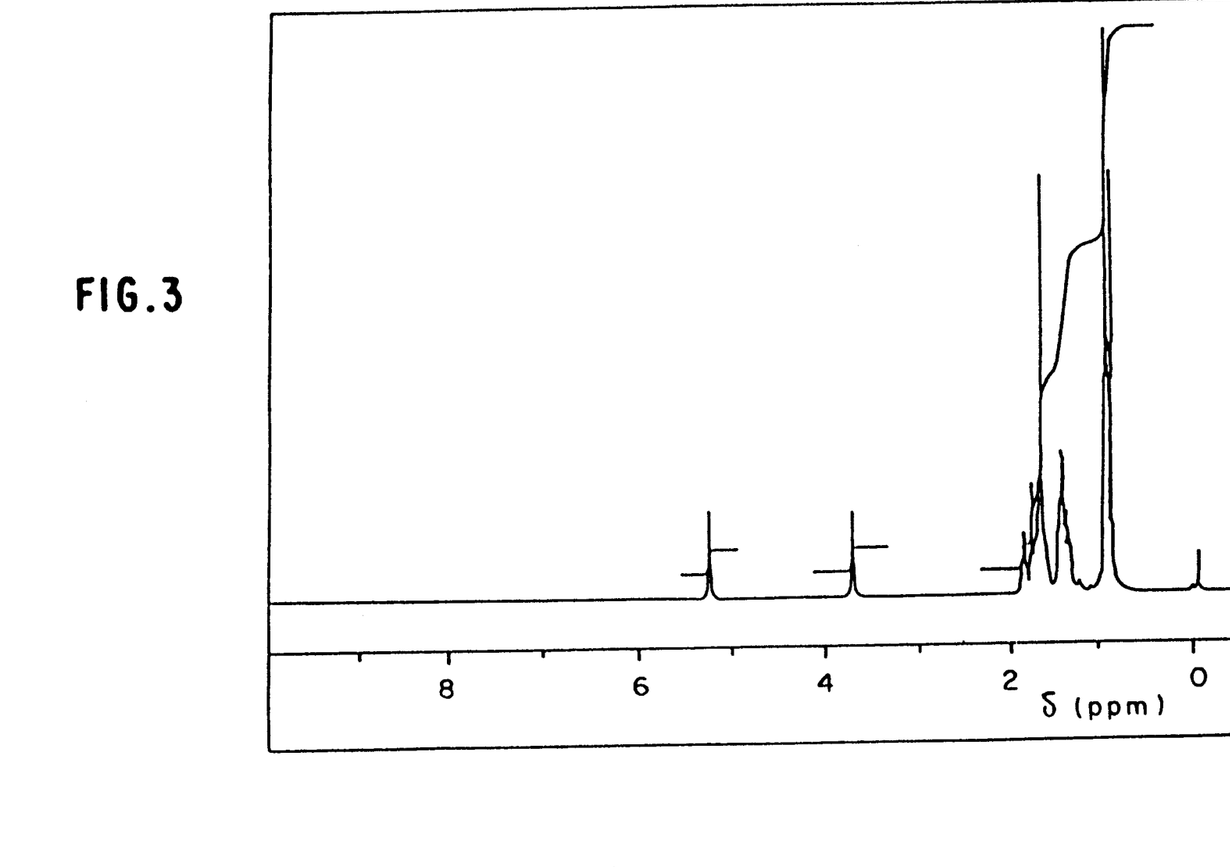
FIG. 3 is a graph showing $^1$H-NMR spectrum of sec-cedrenol.
Figure 4:
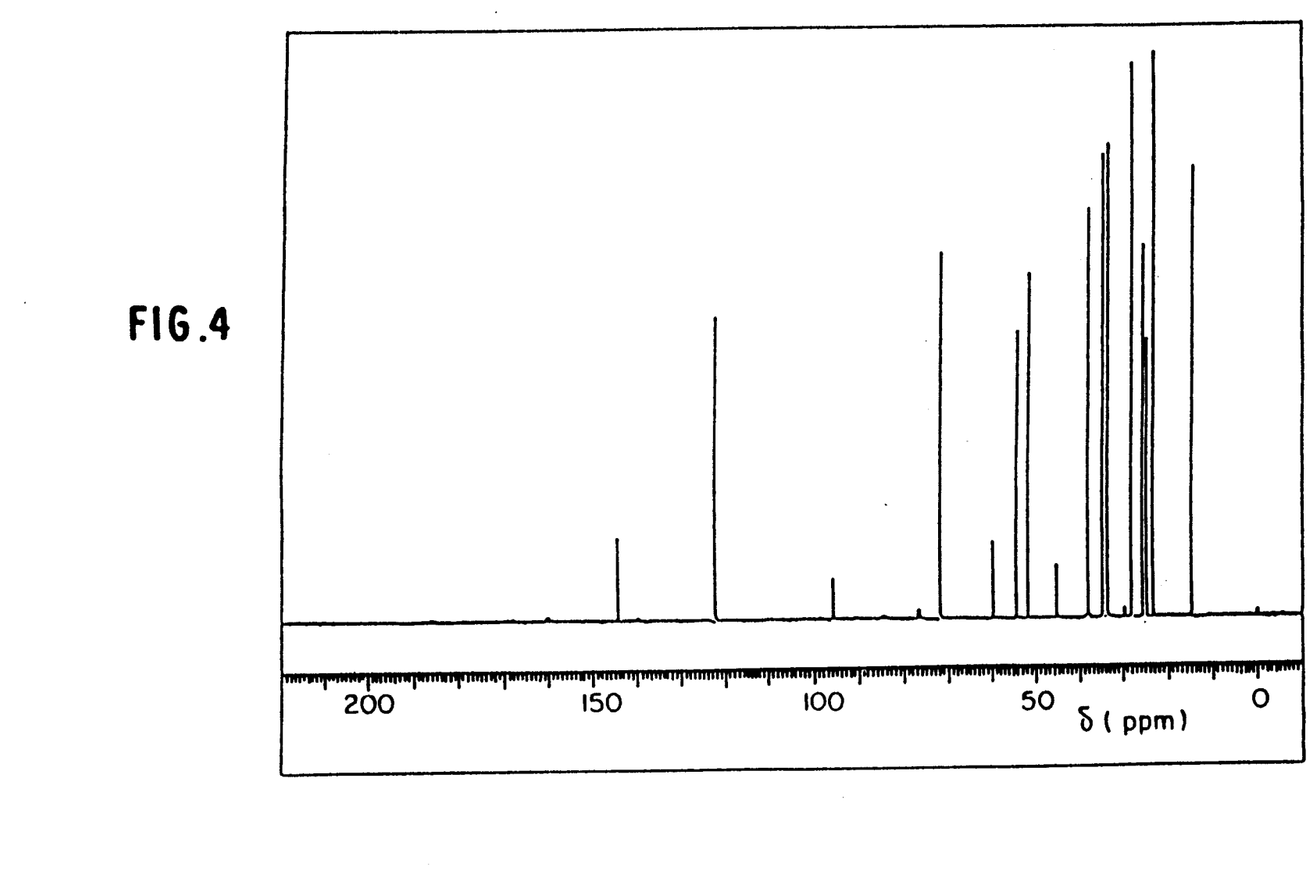
FIG. 4 is a graph showing $^{13}$C-NMR spectrum of sec-cedrenol.

After purifying the product obtained in Example 1, its analysis and identification were carried out and, as a result, it was confirmed that sec-cedrenol was produced. Among analytical and identification data, EI-MS spectrum is shown in FIG. 1, IR spectrum (KBr) is shown in FIG. 2, $^1$H-NMR spectrum (CDCl$_3$, 400 MHz) is shown in FIG. 3, and $^{13}$C-NMR spectrum is shown in FIG. 4.

EXAMPLE 3

The strain KSM-7358 obtained in Example 1 was cultured on a slant culture medium (Medium B, shown below) at 30° C. for 3 days. A portion of the thus grown cells were inoculated into a 500 ml Sakaguchi'flask (a shouldered-type culture flask) containing 50 ml of Medium C shown below which contains 0.5% of α-cedrene, and the thus inoculated cells were cultured at 30° C. for 2 days. A 0.5 ml portion of the thus prepared seed culture was inoculated into 50 ml of the Medium C containing 0.5% of α-cedrene (in 500 ml Sakaguchi'es flask), followed by 4 days of shaking culture at 30° C.

Figure 5:
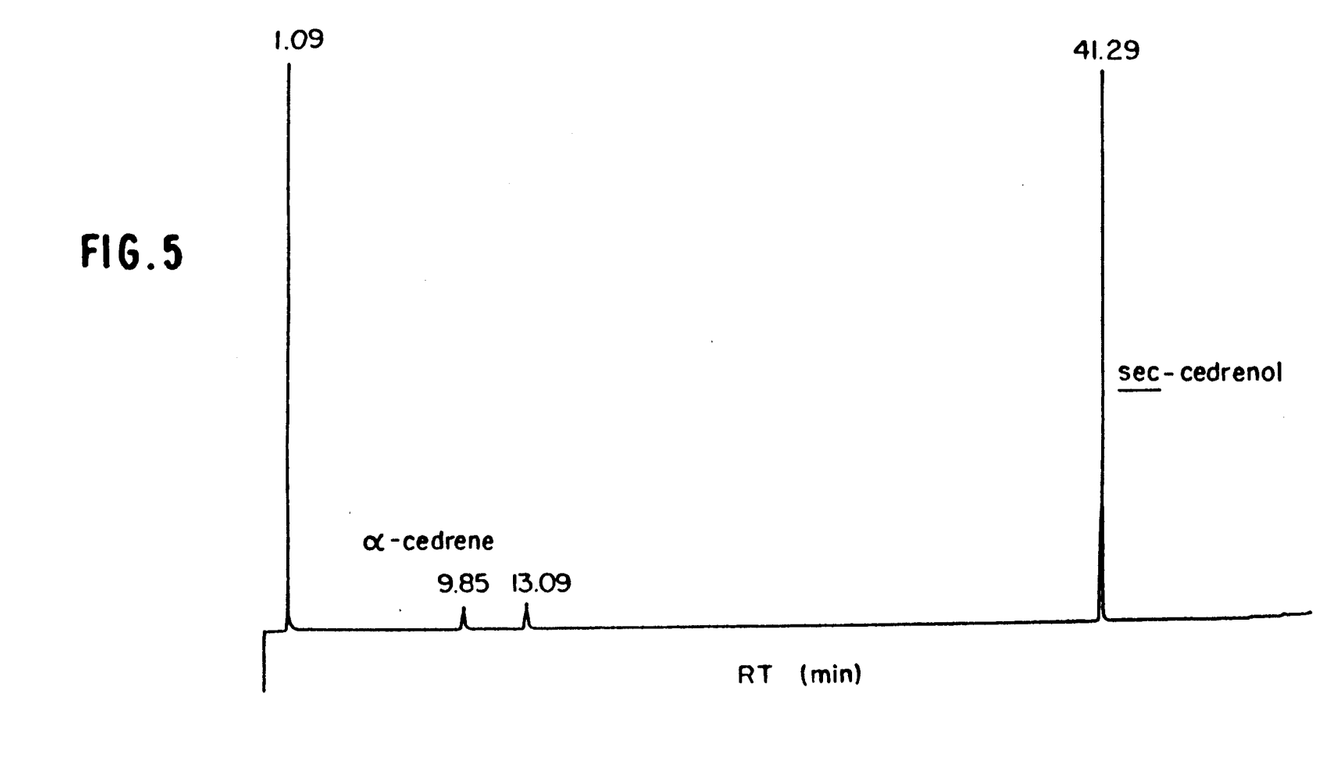
FIG. 5 is a graph showing a gas chromatogram of sec-cedrenol (resting cell reaction).

Thereafter, the resulting culture broth was extracted with hexane, and a portion of the hexane-soluble fraction was applied to gas chromatography to find production of sec-cedrenol with an yield of 25 mg (FIG. 5).

Gas chromatographic analysis of the sample was carried out using HP5880 gas chromatograph (Hewlet-Packard Co., Calif., U.S.A.) equipped with a flame ionization detector and a capillary column (0.25 mm×25 m) coated with Carbowax 20M at helium carrier flowing of 25 ml/min. The temperature program was 80° C. for 10 minutes, 80° to 150° C. at 2° C./min., 150° to 220° C. at 10° C./min., and finally 220° C. for 5 minutes.

| Medium B: | |
|---|---|
| Polypeptone (a casein peptone) | 17 g |
| Polypeptone S (a soybean peptone) | 3 g |
| K$_2$HPO$_4$ | 2.5 g |
| Glucose | 2.5 g |
| NaCl | 5 g |
| Agar | 15 g |

Fill up to 1 liter with deionized water (pH after sterilization: 7.1 to 7.5).

| Medium C: | |
|---|---|
| Na$_2$SO$_4$ | 0.71 g |
| NH$_4$NO$_3$ | 3.5 g |
| FeCl$_3$.6H$_2$O | 0.01 g (separately sterilized) |
| MgCl$_2$.6H$_2$O | 0.17 g (separately sterilized) |
| CaCl$_2$.2H$_2$O | 0.1 g (separately sterilized) |

Fill up to 1 liter with 50 mM phosphate buffer (pH 7).

EXAMPLE 4

(1) Three 500 ml Sakaguchi's flasks, each containing 100 ml of Medium D shown below, were inoculated with strain KSM-7358 which has been slant-cultured using the aforementioned Medium B at 30° C. for 3 days.

After culturing with shaking at 30° C. for 2 days, 300 ml of the resulting culture broth was subjected to centrifugation at 5° C. for 10 minutes (12,000 x g). Thereafter, the thus collected cells were washed twice with 300 ml for each of cold 50 mM phosphate buffer (pH 7.0) and then suspended in an appropriate volume of the same buffer to prepare a resting cell suspension having a cell density of about 40 in terms of absorbance at 600 nm.

| Medium D: | |
|---|---|
| Polypeptone (a casein peptone) | 17 g |
| Polypeptone S (a soybean peptone) | 3 g |
| K$_2$HPO$_4$ | 2.5 g |
| Glucose | 2.5 g |
| NaCl | 5 g |

Fill up to 1 liter with deionized water (pH after sterilization, 7.1 to 7.5).

Figure 6:
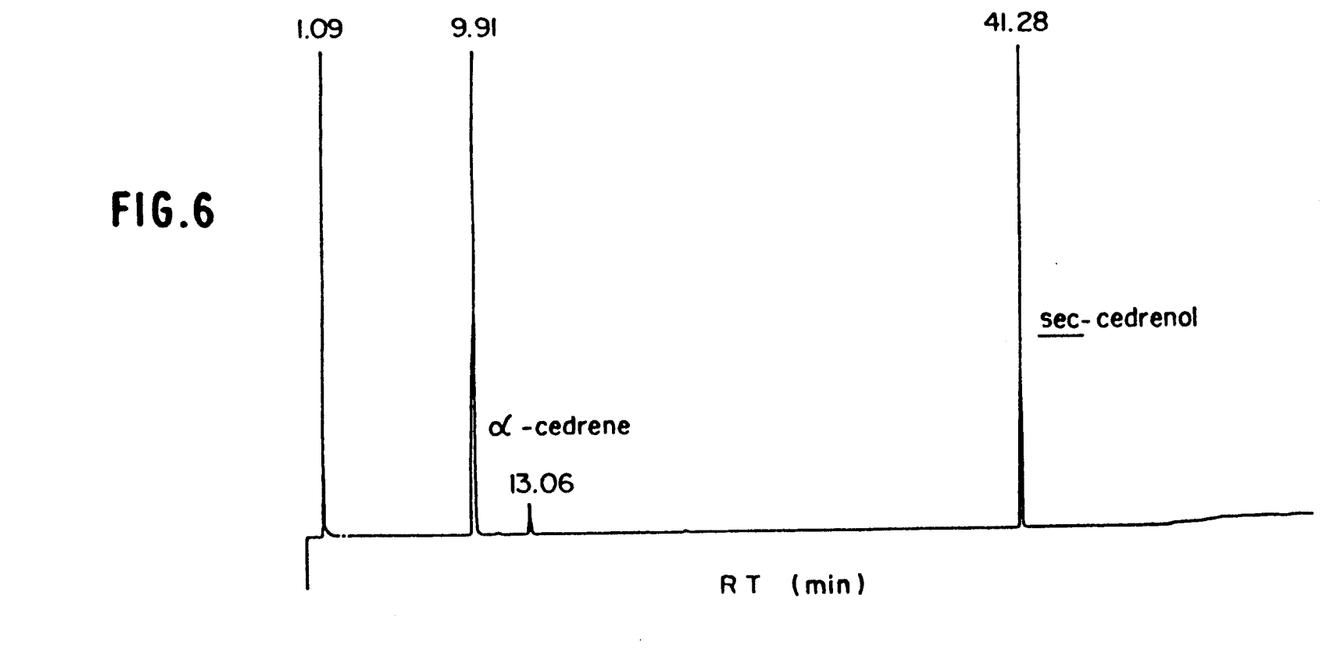
FIG. 6 is a graph showing a gas chromatogram of sec-cedrenol (after 4 days of culturing).

(2) A 500 ml conical flask was charged with 50 ml of the resting cell suspension obtained in the above step (1) and then with 250 mg of α-cedrene, and the flask was shaken at 130 rpm on a rotary shaker at 30° C. for 2 days. The thus obtained reaction mixture was extracted with 50 ml of hexane, and a portion of the resulting extract was applied to gas chromatography to confirm formation of sec-cedrenol (FIG. 6). Thereafter, 200 mg of purified sec-cedrenol was obtained by separating the product from the hexane extract by means of silica gel chromatography and crystallizing the separated sample at a low temperature.

EXAMPLE 5

The strain KSM-7358 obtained in Example 1 was slant-cultured using the aforementioned Medium B at 30° C. for 3 days. A portion of the thus grown cells were inoculated into a 500 ml Sakaguchi's flask containing 50 ml of the aforementioned Medium D. After culturing at 30° C. for 1 day, α-cedrene was added to the cultured broth and the culturing was continued for additional 2 days.

Thereafter, the resulting culture broth was extracted with hexane, and a portion of the hexane-soluble fraction was applied to gas chromatography to find production of sec-cedrenol with an yield of 80 mg.

EXAMPLE 6

The strain KSM-7358 obtained in Example 1 was slant-cultured using the aforementioned Medium B at 30° C. for 3 days. A portion of the thus grown cells were transferred into a 500 ml Sakaguchi's flask containing 100 ml of the aforementioned Medium D and cultured on a shaker at 30° C. for 2 days. A 25 ml portion of the culture broth thus obtained was inoculated into a previously sterilized 5 liter jar fermentor containing 2.5 liters of Medium D, and culturing was carried out at an aeration rate of 1 vvm and at an agitation rate of 400 rpm. After 24 hours of the culturing, 1.4 liters of a resting cell suspension was prepared in the same manner as in Example 4. 7 g of α-cedrene was added to the cell suspension and the mixture was incubated at 30° C. under aeration and agitation conditions of 1 vvm and 400 rpm, respectively. Thereafter, 7 g portions of α-cedrene were added to the incubating cell suspension with intervals of 24 hours. In this way, 24 g of sec-cedrenol was obtained from 35 g of α-cedrene in total.

EXAMPLE 7

A 200 ml four-necked flask equipped with a stirrer, a thermometer and a dropping funnel was charged with 1.95 g of pyridinium chlorochromate and 30 ml of dichloromethane, and the mixture was kept at 25° C. To this was added dropwise 30 ml of a dichloromethane solution containing 1 g of sec-cedrenol over about 10 minutes with stirring. After stirring at 25° C. for 1 hour, the resulting reaction mixture was applied to a column of silica gel (50g; Wakogel C-200) and eluted with dichloromethane, and, thereafter, the elute was concentrated to obtain 0.8 g of cedrenone.

EI-MS spectrum, IR spectrum and ¹H-NMR spectrum of this product coincided with those of an authentic sample of cedrenone.

While the invention has been described in detail and with reference to specific examples thereof, it will be apparent to one skilled in the art that various changes and modifications can be made therein without departing from the spirit and scope thereof.

What is claimed is:

1. A process for producing cedrenone of the formula:

which comprises
A) culturing Rhodococcus sp. KSM-7358 in a nutrient medium containing α-cedrene under conditions effective to produce sec-cedrenol of the formula:

B) recovering said sec-cedrenol;
C) oxidizing the recovered sec-cedrenol to obtain cedrenone; and
D) recovering the cedrenone.

2. The process of claim 1, wherein said sec-cedrenol is oxidized with pyridinium chlorochromate.

3. A process for producing sec-cedrenol of the formula:

comprising
A) culturing Rhodococcus sp. KSM-7358 in a nutrient medium containing α-cedrene under conditions effective to produce said sec-cedrenol; and
B) recovering the sec-cedrenol.

* * * * *